US007053187B2

(12) United States Patent
Wang

(10) Patent No.: US 7,053,187 B2
(45) Date of Patent: May 30, 2006

(54) SPERM-SPECIFIC MONOCLONAL ANTIBODY, MABC

(75) Inventor: Kangsheng Wang, Rowland Heights, CA (US)

(73) Assignee: Gioagri Corporation, City of Industry, CA (US)

( * ) Notice: Subject to any disclaimer, the term of this patent is extended or adjusted under 35 U.S.C. 154(b) by 0 days.

(21) Appl. No.: 09/781,046

(22) Filed: Feb. 8, 2001

(65) Prior Publication Data

US 2002/0004240 A1 Jan. 10, 2002

Related U.S. Application Data

(63) Continuation-in-part of application No. 09/537,861, filed on Mar. 28, 2000.

(51) Int. Cl.
C07K 16/00 (2006.01)
C12P 21/08 (2006.01)

(52) U.S. Cl. .................. 530/388.1; 530/387.1
(58) Field of Classification Search ............. 530/388.1, 530/388.15, 388.21, 389.1, 387.1
See application file for complete search history.

(56) References Cited

U.S. PATENT DOCUMENTS

| 5,428,132 | A | 6/1995 | Hirsch et al. | |
|---|---|---|---|---|
| 5,521,291 | A | 5/1996 | Curiel et al. | |
| 5,744,335 | A | 4/1998 | Wolff et al. | 435/458 |
| 6,063,630 | A | 5/2000 | Treco et al. | 435/463 |
| 2002/0004240 | A1 | 1/2002 | Wang | |

FOREIGN PATENT DOCUMENTS

| CN | 1208600 | 2/1999 |
|---|---|---|
| EP | 0 431 839 A1 | 6/1991 |
| EP | 0 431 839 B1 | 6/1991 |
| EP | 0 846 772 A1 | 10/1998 |
| RU | 2081914 | 6/1997 |
| WO | WO 90/08192 | 7/1990 |
| WO | WO 93/24626 | 12/1993 |
| WO | WO 97/11597 | 4/1997 |
| WO | WO 99/38991 | 8/1999 |
| WO | WO 99/40213 | 8/1999 |
| WO | WO 99/42569 | 8/1999 |
| WO | WO 00/08924 | 2/2000 |
| WO | WO 00/29602 | 5/2000 |
| WO | WO 01/73094 A2 | 10/2001 |

OTHER PUBLICATIONS

Yan et al.; Characterization of Sperm Agglutinating Monoclonal Antibody and Purification of the Human Sperm Antigen, 1986, Int. J. Fertil. 31: 77-85.*
Nakamura et al.; Identification and Characterization of a Sperm Peptide Antigen Recognized By A Monoclonal Antisperm Autoantibody Derived from a Vasectomized Mouse, 1994, Biochemical And Biophysical Research Communications, vol. 205: 1503-1509.*
Naz et al.; Antibodies to sperm-specific human FA-1 inhibit in vitro fertilization in rhesus monkeys: delvelopment of a simian model for testing of anti-FA-1 contraceptive vaccine, 1994, Journal of Reproductive Immunology 27: 111-121.*
Kim et al.; Effects of Expermentally Generated Bull Antisperm Antibodies on in Vitro Fertilization, 1999, Biology of Reproduction 60:1285-1291.*
Smith, K. (1999) "Sperm Cell Mediated Transgenesis: A Review," *Animal Biotechnology* 10(1&2): 1-13.
Gandolfi, F. (1998) "Spermatozoa, DNA Binding and Transgenic Animals," *Transgenic Research* 7(3): 147-155.
Spadafora, C. (1998) "Sperm Cells and Foreign DNA: a controversial relation," *BioEssays* 20(11): 955-964.
Lavitrano, M., et. al. (1999) "Human Decay Accelerating Factor Transgenic Pigs Obtained by Sperm Mediated Gene Transfer," *Transplantation Proceedings* 31: 972-974.
Liu, X.Y., et. al. (1999) Association of Foreign DNA with Sperm of Gilthead Seabream, *Sparus aurata*. After Sonication, Freezing, and Dimethyl Sulfoxide Treatments, *Marine Biotechnology* 1: 175-183.
Hasebe, M., et al. (1998) "An Attempt to Produce Transgenic Chicken Mediating Sperm Cells as Vectors," *Journal of Applied Animal Research* 14: 143-150.
Rottmann, O.J., et. al. (1996) "Liposome Mediated Gene-Transfer via Sperm Cells. High Transfer Efficiency and Persistence of Transgenes by Use of Liposomes and Sperm Cells and a Murine Amplification Element," *J. Animal Breed. Genet.* 113: 401-411.
Sperandio, S., et. al. (1996) "Sperm Mediated DNA Transfer in Bovine and Swine Species," *Animal Biotechnology*, 7: 59-77.
Maione, B., et. al., (1998) "Sperm-Mediated Gene Transfer in Mice," *Molecular and Development* 50:406-409.
Maione, B., et. al. (1997) "Activation of Endogenous Nucleases in Mature Sperm Cells upon Interaction with Exogenous DNA," *DNA and Cell Biology* 16(9): 1087-1097.
Birnstiel, M. and Busslinger, M., (1989) "Dangerous Liaisons: Spermatozoa as Natural Vectors for Foreign DNA?," *Cell* 57: 701-702.
Dickson, D. (1989) "'Dangerous' Liasons in Cell Biology" *Science* 244 1539-1540.

(Continued)

Primary Examiner—Joseph Woitach
Assistant Examiner—Thaian N. Ton
(74) Attorney, Agent, or Firm—Michael J. Wise; Perkins Coie LLP

(57) ABSTRACT

A method and vector system for delivering of a gene into a human stem cell for therapeutic uses is disclosed. The method includes linking a therapeutic gene to human sperm cells through a linker and fertilizing a human oocyte. The resulting zygote may then be cultured and established as human embryonic stem cells, which may later be differentiated into different types of cells for transplantation into the human body.

2 Claims, 12 Drawing Sheets

OTHER PUBLICATIONS

Brinster, R.L., et. al., (1989) "No Simple Solution for Making Transgenic Mice," *Cell* 59:239-241.

Tsai, H.J., et. al., (1997) "Sperm as a carrier to introduce an exogenous DNA fragment into the oocyte of Japanese abalone (Haliotis divorsicolor suportexta)," *Transgenic Research* 6(1): 85-95.

Gagne, M. B., et. al., (1991) "Electroporation of Bovine Spermatozoa to Carry Foreign DNA in Oocytes," *Molecular Reproduction and Development* 29: 6-15.

Lavitrano, M., et. al., (1989) "Sperm Cells as Vectors for Introducing Foreign DNA into Eggs: Genetic Transformation of Mice," *Cell* 57: 717-723.

Wall, R.J., et. al. (1992) Making Transgenic Livestock, Genetic Engineering on a Large Scale, *Journal of Cellular Biochemistry* 49: 113-120.

Francolini, M., et. al (1993) Evidence for Nuclear Internalization of Exogenous DNA into Mammalian Sperm Cells, *Mol. Reprod. Devel.* 34: 133-139.

Lavitrano, M., et al. (1992) The Interaction Between Exogenous DNA and Sperm Cells, *Mol. Reprod. Devel.*, 31: 161-169.

Pursel, V. G., et.al. (1989) Genetic Engineering of Livestock, *Science* 244: 1281-1288.

Ward, K., (1991) The Application of Transgenic Techniques for the Improvement of Domestic Animal Productivity, *Current Opinion in Biotechnology* 2: 834-839.

Lonnerdal, B. (1996) Recombinant Human Milk Proteins—An Opportunity and a Challenge, *American Journal of Clinical Nutrition* 63: 622-626.

Cozzi, E., et. al. (1994) Expression of Human Decay Accelerating Factor in Transgenics Pigs, *Transplantation Proceedings*. 26: 1402-1403.

Etherton, T.D., et. al. (1993) Mechanism by which Somatotropin Decreases Adipose Tissue Growth, *American Journal of Clinical Nutrition* 58 (Supp.): 287S-295S.

Hurley, Carolyn K. et al., (1997) HLA Typing by Molecular Methods, *Manual of Clinical Laboratory Immunology* 140: 1098-1111.

Marijt, Erik A.F., et al (1993) Multiple Minor Histocompatibility Antigen Disparities Between a Recipient and Four HLA-Identical Potential Sibling Donors for Bone Marrow Transplantation. *Human Immunology*, 37, 221-228.

Gardner, David K., et al. Culture and selection of viable blastocysts: a feasible proposition for human IVF?, *Human Reproduction Update* 1997, vol. 3, No. 4, pp. 367-382.

Barnes, Frank L. et al., Blatocyst development and birth after in-vitro maturation of human primary oocytes, intracytoplasmic sperm injection and assisted hatching, *Human Reproduction*, vol. 10 No. 12, pp. 3243-3247, 1995.

Katovich, Hurley et al., Histocompatibility: Interpretation and Correlation of HLA Typing for Bone Marrow Transplantation, http: www.bminfo.org/bmt/topics/htm/dnatype.htm, Oct. 24, 2000, pp. 1-12.

What is HLA, http://www.innogenetics.com/Website/Website.nsf/7df3b6bb9c0862e8c12567380052687f/e, Oct. 24, 2000, pp. 1-6.

McKenzie, John, Life-Saving Embryo? http://www.abcnews.go.com/onair/WorldNewsTongiht/wnt001003_testubebaby_feature.ht, Oct. 25, 2000, pp. 1-2.

Human embryonic stem cell and embryonic germ cell lines. http://www.ncbi.nlm.nih.gov/entrez/query.fcgi?cmd=Retrive&db—PubMed&list_uids-10.6. Oct. 25, 2000, p. 1.

Neural differentiation of rhesus embryonic stem cells. http://www.ncbi.nlm.nih.gov/entrez/query.fcgi?cmd-Retrieve&db-PubMedlist_uids-95.2. Oct. 25, 2000, p. 1.

Isolation of a primate embryonic stem cell line. http://www.ncbi.nlm.nih.gov/entrez/query.fcgi?cmd-Retrieve&db-PubMed&list_uids-75.4, Oct. 25, 2000, pp. 1-2.

Histcocompatibility: Interpretation and Correlation of HLA Typing for Bone Marrow Transplantation. http://www.bmtinfo.org/bmt/topics/htm/type_b.htm. Oct. 24, 200, pp./1-9.

Qu, Zhuqing, et al., Development of Approaches to Improve Cell Survival in Myoblast Transfer Therapy, *The Journal of Cell Biology*, vol. 142, No. 5, Sep. 7, 1998, 1257-1267.

Yoder, Mervin C., et al., *In vivo* repopulating hematopoietic stem cells are present in the murine yolk sac at day 9.0 postcoitus, *Proc. Natl. Acad. Sci USA*, vol. 94, pp. 6776, 6780, Jun. 1997.

Kolosov, E., et al., Functional Characteristics of ES Cell-derived Cardiac Precursor Cells Identified by Tissue-specific Expression of the Green Fluorescent Protein, *The Journal of Cell Biology*, vol. 143, No. 7, Dec. 28, 1998, 2045-2056.

Gardner, David K., et al., Culture and transfer of human blastocysts increases implantation rates and reduces the need for multiple embryo transfers, *Fertility and Sterility*, vol. 69, No. 1, Jan. 1998, pp. 84-88.

Slager, H.G., et al., Transforming Growth Factor-β in the Early Mouse Embryo: Implications for the Regulation of Muscle Formation and Implantation, *Developmental Genetics* 14:212-224 (1993).

Bain, Gerard, et al., Embryonic Stem Cells Express Neuronal Properties *In Vitro*, *Developmental Biology* 168, 342-357 (1995).

Rohwedel, J., et al., Muscle Cell Differentiation of Embryonic Stem Cells Reflects Myogenesis in Vivo: Developmentally Regulated Expression of Myogenic Determination Genes and Functional Expression of Ionic Currents, *Developmental Biology* 164, 87-101(1994).

NT2PrecursorCells, Instruction Manual, Catalog #204101, Revision #079006, 1999.

Li, Meng, et al., Generation of purified neural precursors from embryonic stem cells by lineage selection,. *Current Biology*, vol. 8, No. 17, 1998.

Thomson, Jmaes A., et al., Embryonic Stem Cell Lines Derived from Human Blastocytes, *Science*, vol. 282, Nov. 6, 1998.

Reubinoff, Benjamin E., et al., Embryonic stem cell lines from human blastocysts: somatic differentiation in vitro. *Nature Biotechnology*, vol. 18, Apr. 2000.

Palacios, Ronald et al., *In vitro* generation of hematopoietic stem cells from an embryonic stem cell line, *Proc. Natl. Acad. Sci. USA*, vol. 92, pp. 7530-7534, Aug. 1995.

Xu, Ming-jiang, et al., Stimulation of Mouse and Human Primitive Hematopoiesis by Murine Embryonic Aorta-Gonad-Mesonephros-Derived Stromal Cell Lines,*Blood*, vol. 92, No. 8 (Sep. 15, 1998), pp. 2032-2040.

Dunnett, Stephen B., et al., Basic Transplantation Methods in Rodent Brain, *Neuromethods*, vol. 36, pp. 133-148.

Castro, Anthony J., et al., Neural Transplantation in the Developing CNS, *Neuromethods*, vol. 36, pp. 169-194.

Barker, Roger A., et al., Preparation of Cell Suspensions for Transplantation, *Neuromethods*, vol. 36, pp. 195-205.

Nikkhah, Guido, et al., Microtransplantation of Nigral Dopamine Neurons A Step-by-Step Recipe, *Neuromethods*, vol. 36, pp. 207-231.

Huard, Johnny, et al., Gene Transfer to Muscle and Spinal Cord Using Herpes Simplex-Based Virus, *Stem Cell Biology and Gene Therapy*, 1998, pp. 179-200.

Gardner, David K. et al., Culture and transfer of human blastocysts increases implantation rates and reduces the need for multiple embryo transfers, *Fertility and Sterility*, vol. 69, No. 1, Jan. 1998.

Klug, Michael G. et al., Genetically Selected Cariomyocytes from Differentiating Embryonic Stem Cells From Stable Intracardiac Grafts, *J. Clin. Invest.*, vol. 98, No. 1, Jul. 1996, 216-224.

Van Hennik, Paula B., et al., Highly Efficient Transduction of the Green Fluorescent Protein Gene in Human Umbilical Cord Blood Stem Cells Capable of Cobblestone Formation in Long-Term Cultures and Multilineage Engraftment of Immunodeficient Mice, *Blood*, vol. 92, Dec. 1, 1998, pp. 4013-4022.

Thomson, James A. et al., Embryonic Stem Cell Lines Derived from Human Blastocysts, *Science*, vol. 282, Nov. 6, 1998, pp. 1145-1147.

Weissman, Irving L. et al., Translating Stem and Progenitor Cell Biology to the Clinic: Barriers and Opportunities, *Science*, vol. 287, Feb. 25, 2000, pp. 1442-1446.

Schuldiner, Maya et al., Effects of eight growth factors on the differentiation of cells derived from human embryonic stem cells, *PNAS*, vol. 97, Oct. 10, 2000, pp. 11307-11312.

Wiles, Michael V. et al., Multiple hematopoietic lineages develop from embryonic stem (ES) cells in culture, *Development III*, 259-267 (1991).

Isacson, Ole et al., Gene Therapy of Huntington's Disease, *Gene Therapy for Neurological Disorders and Brain Tumors*, pp. 427-443.

Pechan, Peter A. et al., Gene Therapy for Ischemic Stroke, *Gene Therapy for Neurological Disorders and Brain Tumors*, pp. 397-408.

Senut, Marie-Claude et al., Gene Transfer for Adult CNS Regeneration and Aging, *Gene Therapy for Neurological Disorders and Brain Tumors*, pp. 345-375.

Bohn, Martha C. et al., Gene Therapies for Parkinson's Disease, *Gene Therapy for Neurological Disorders and Brain Tumors*, pp. 377-395.

Medin, Jeffrey A. et al., *Gene Therapy of Enzyme and Immune Deficiencies in the Hemopoietic System*, pp. 386-413.

Kaye, Edward M., Gene Therapy for Lysosomal Storage Diseasese, *Gene Therapy for Neurological Disorders and Brain Tumors*, pp. 409-418.

Davar, Gudarz, Gene Therapy for Pain, *Gene Therapy for Neurological Disorders and Brain Tumors*, pp. 419-426.

Chandran, Siddharthan et al., Neural Stem Cells for Transplantation, *Neuromethods*, vol. 36: pp. 41-54.

Wolf, Eckhard et al., Transgenic technology in farm animals—progress and perspectives, *The Experimental Physiology* (2000) pp. 615-625.

Squires, E.J., Status of Sperm-mediated Delivery Methods for Gene Transfer, 1999, *Transgenic Animals in Agriculture*, pp. 87-95.

Gandolfi, F., Sperm-Mediated Transgenesis, 1999, *Theriogenology* 53: 127-137, 2000.

Chang, Il-Kuk et al., Production of Germline Chimeric Chickens by Transfer of Cultured Primordial Germ Cells, *Cell Biology International*, 1997, vol. 21, No. 8, 495-499.

Wallen-Ohman, Marie et al., Ligation of MHC class 1 induces apoptosis in human pre-B cell lines, in promyelocytic cell ines and in CD40-stimulated mature B cells, *International Immunology*, vol. 9, No. 4, pp. 599-606.

Chang et al., "Effective generation of transgenic pigs and mice by linker based sperm-mediated gene transfer," manuscript submitted to BMC Biotech on Nov. 3, 2001.

Brackett et al., Uptake of Heterologous genome by mammalian spermatozoa and its transfer to ova through fertilization, PNAS (1971) 68:353-357.

Perry, AC. et al., Mammalian Transgenesis by intracytoplasmic sperm injection., Science (1999) 284: 1180-1183.

Carballada R., Regulation of foreign DNA uptake by mouse spermatozoa, Exp Cell Research 2001, 262: 104-113.

International Search Report for PCT International Application No. PCT/US02/02895, dated Oct. 7, 2003, 7 pages.

International Search Report for PCT International Application No. PCT/US02/40492, dated Jun. 5, 2003, 4 pages.

International Search Report for PCT International Application No. PCT/US01/07018, dated Dec. 3, 2002, 5 pages.

Anwer, Khursheed et al., "Targeted Gene Delivery: A Two-Pronged Approach", *Critical Reviews in Therapeutic Drug Carrier Systems*, 17(4), pp. 377-424 (2000).

Bookbinder, L.H. et al., Tissue- and Species-Specific Express of sp56, a Mouse Sperm Fertilization Protein, *Science*, vol. 269, pp. 86-89 (1995).

Burks, D.J. et al., "Interaction of a Tyrosine Kinase from Human Sperm with the Zona Pellucida at Fertilization", *Science*, vol. 269, pp. 83-86 (1995).

Chang, Keejong et al., "Effective generation of transgenic pigs and mice by linker based sperm-mediated gene transfer", BMC Biotechnology 2002, 2:5, http://www.biomedcentral.com/1472-6750/2/5.

Cheng, Alice et al., "Sperm-Egg Recognition in the Mouse: Characterization of sp56, A Sperm Protein Having Specific Affinity for ZP3", *The Journal of Cell Biology*, vol. 125, No. 4, pp. 867-878 (1994).

Cornwall, Gail A. et al., Inhibition of the Mouse Sperm Surface α-D-Mannosidase Inhibits Sperm-Egg Binding in Vitro, *Biology of Reproduction*, vol. 44, No. 5, pp. 913-921 (1991).

Fusi, F.M., "In vitro production of human anti-sperm antibodies: effect of an oligoclonal antibody (F6) on sperm-egg interaction," Journal of Reproductive Immunology, vol. 29, No. 2, 1995, pp. 135-147.

Gao, Zeren et al., "Species Diversity in the Structure of Zonadhesin, a Sperm-specific Membrane Protein Containing Multiple Cell Adhesion Molecule-like Domains", *The Journal of Biological Chemistry*, vol. 273, No. 6, pp. 3415-3421 (1998).

Gougoulidis, Tiki et al., "Inhibition of Bovine Sperm-Oocyte Fusion by the Carbohydrate GalNAc", *Molecular Reproduction and Development*, vol. 54, No. 2, pp. 179-185 (1999).

Hardy, Daniel M. et al., "A Sperm Membrane Protein That Binds in a Species-specific Manner to the Egg Extracellular Matrix Is Homologous to von Willebrand Factor", *The Journal of Biological Chemistry*, vol. 270, No. 44, pp. 26025-26028 (1995).

Kadam, Arjun L. et al., "Fertilization antigen (FA-1) completely blocks human sperm binding to human zona pellucida: FA-1 antigen may be a sperm receptor for zona pellucida in humans", *Journal of Reproductive Immunology*, vol. 29, No. 1, pp. 19-30 (1995).

Kalab, Petr et al., "p95, the Major Phosphotyrosine-containing Protein in Mouse Spermatozoa, Is a Hexokinase with Unique Properties", *The Journal of Biological Chemistry*, vol. 269, No. 5, pp. 3810-3817 (1994).

Kameda, Kinu et al., "Comparative Studies of the Antigens Recognized by Sperm-Immobilizing Monoclonal Antibodies", *Biology of Reproduction*, vol. 46, pp. 349-357 (1992).

Lacy, H. Marie et al., "Sperm protein 17 is expressed on normal and malignant lymphocytes and promotes heparan sulfate-mediated cell-cell adhesion", *Blood*, vol. 98, No. 7, pp. 2160-2165 (2001).

Lu, Qingxian et al., "Sperm from β1,4-galactosyltransferase-null mice are refractory to ZP3-induced acrosome reactions and penetrate the zona pellucida poorly", *Development*, vol. 124, pp. 4121-4131 (1997).

Miller, David J. et al., "Complementarity between sperm surface β-1,4-galactosyl-transferase and egg-coat ZP3 mediates sperm-egg binding", *Nature*, vol. 357, No. 6379, pp. 589-593 (1992).

Morawatz, R., Written Opinion, issued on Jun. 27, 2002 by PTO regarding International Application No. PCT/US01/07018, which claims the priority to U.S. Appl. No. 09/537,861, 9 pages.

Mori, Kazumasa et al., "Blocking of human fertilization by carbohydrates", *Human Reproduction*, vol. 8, No. 10, pp. 1729-1732 (1993).

Pain, B. et al., "Chicken Embryonic Stem Cells and Transgenic Strategies." Cells Tissues Organs. 1999, vol. 165, pp. 212-219.

Pereira, Ben M.J. et al., "Rat Sperm Surface Mannosidase Is First Expressed on the Plasma Membrane of Testicular Germ Cells", *Biology of Reproduction*, vol. 59, No. 6, pp. 1288-1295 (1998).

Richardson, Richard T. et al., "Sequence of a Rabbit Sperm Zona Pellucida Binding Protein and Localization during the Acrosome Reaction", *Developmental Biology*, vol. 165, No. 2, pp. 688-701 (1994).

Rivkin, Eugene et al., "Molecular Cloning of Rat Sperm Galactosyl Receptor, a C-Type Lectin With In Vitro Egg Binding Activity", *Molecular Reproduction and Development*, vol. 56, No. 3, pp. 401-411 (2000).

Shaha, Chandrima et al., "Monoclonal Antibody Against a Human Sperm Protein Recognizes Multiple Epitopes on Rabbit and Human Sperm and Blocks Sperm Function," HYBRIDOMA, vol. 12, No. 6, 1993, pp. 709-718.

Töpfer-Petersen E. et al., "Spermadhesins: A new protein family. Facts, hypotheses and perspectives", *Andrologia*, vol. 30, No. 4-5, pp. 217-224 (1998).

Töpfer-Petersen E. et al., "Sperm-associated protein candidates for primary zona pellucida-binding molecules: structure-function correlations of boar spermadhesins", *Journal of Reproduction and Fertility Supplement 50*, pp. 55-61 (1996), abstract only.

Uherek, Christoph et al., "DNA-carrier proteins for targeted gene delivery", *Advanced Drug Delivery Reviews*, 44(2-3), pp. 153-166 (2000).

Varga, Csanad M. et al., "Receptor-Mediated Targeting of Gene Delivery Vectors: Insights from Molecular Mechanisms for Improved Vehicle Design", *Biotechnology and Bioengineering*, vol. 70, No. 6, pp. 593-605 (2000).

Yamasaki, Noriyuki et al., "Expression of the Rabbit Sperm Protein Sp17 in Cos Cells and Interaction of Recombinant Sp17 With the Rabbit Zona Pellucida", *Molecular Reproduction and Development*, vol. 40, No. 1, pp. 48-55 (1995).

Yan, Yuan Chang et al., "Characterization of cDNA encoding a human sperm membrane protein related to A4 amyloid protein", *Proc. Natl. Acad. Sci.*, vol. 87, pp. 2405-2408 (1990).

Zani, Massimo, "The Mechanism of Binding of Exogenous DNA to Sperm Cells: Factors Controlling the DNA Uptake," Experimental Cell Research, vol. 217, No. 1, 1995, pp. 57-64.

Zhu, Xiaolong et al., "Fertilization antigen-1: cDNA cloning, testis-specific expression, and immunocontraceptive effects", *Proceedings of the National Academy of Sciences*, vol. 94, No. 9, pp. 4704-4709 (1997).

* cited by examiner

SPERM-SPECIFIC MONOCLONAL ANTIBODY, MABC

RELATED APPLICATIONS

This application is a continuation-in-part application claiming priority to U.S. patent application Ser. No. 09/537,861, filed on Mar. 28, 2000. U.S. application Ser. No. 09/537,861 is hereby incorporated by reference as if fully set forth herein.

FIELD OF THE INVENTION

The field of the present invention relates to vector systems for gene and stem cell therapy. In particular, it relates to a method and system for introducing a gene into a human stem cell to be used for therapeutic purposes.

BACKGROUND OF THE INVENTION

Various diseases originate from defective genes that are either inherited or modified during life by environmental agents. Examples of these diseases include different forms of cystic fibrosis, Tay Sachs, sickle cell anemia, Duchenne muscular dystrophy, cancer, hemophilia, or LDL receptor deficiency. In addition, certain conditions are caused by the imbalance or lack of certain hormones or growth factors in the body stemming from damage to a particular organ. For example, kidney dialysis patients are often anemic because the damaged kidneys do not produce sufficient erythropoietin to adequately stimulate production of an appropriate level of red blood cells. Gene therapy or gene replacement therapy promises, not only a treatment, but also a potential cure for these diseases by replacing defective genes or by augmenting production of certain gene products.

Common vectors for introducing the therapeutic gene or nucleic acid include viral and non-viral vectors. Although viral delivery systems have been considered to be most efficient in delivering genes to cells, it may be limited because of a risk of triggering inflammatory or immunogenic responses. Forbes, S. J., "Review Article: Gene Therapy in Gastroenterology and Hepatology," *Ailment Pharmacol. Ther.* 11:823–826 (1997). The risk is exemplified by the death of Jesse Gelsinger, a volunteer who died on Sep. 17, 1999 while participating in a gene therapy clinical trial at the Institute for Human Gene Therapy, University of Philadelphia. His death has fueled the controversy over the use and safety of gene therapy. The trial was directed to treat ornithine transcarbmylase (OTC) using a modified adenoviral vector. The administration, however, of the vector to Gelsinger "initiated an unusual and deadly immune-system response that led to multiple organ failure and death." See Preliminary Findings, The Institute of Human Gene Therapy, University of Pennsylvania Health System, Dec. 2, 1999. Although adenoviral vectors offer several advantages over other viral vectors in that they can infect a wide range of cells and are not limited to replicating cells, as are retroviral vectors, adenoviral vectors may activate the immune system, as seen in the Gelsinger's case, such that the initial does or repeated introduction may become less effective, if not life threatening. See also Forbes, S. J., supra. Because other gene therapy vectors such as retrovirus or liposomes are generally foreign molecules, they similarly trigger the immune reaction and decrease the effectiveness of the therapy.

In addition to gene therapy, stem-cell based therapies are promising treatments for alleviating certain diseases such as neurodegenerative diseases, hematopoetic diseases and cancers, or muscular dystrophies. For these types of diseases, stem cells that have the ability to differentiate into a specific cell types may be grown in culture and transplanted into, for example, the central nervous system, the muscles, or the bone marrow to regenerate atrophied or ablated tissues. Current protocols for stem cell-based therapies are also disadvantageous because of the potential host immune response to the graft stem cells. In addition, it is also difficult to introduce a therapeutic gene into a human stem cell if such a therapeutic gene would be desirable.

Thus, there exists a need to enhance the safety and efficiency of gene therapy vectors that addresses the complexities of interacting with the immune system and the ease with which a therapeutic gene can be introduced into the body.

SUMMARY OF THE INVENTION

The present invention provides for a method and a vector system for delivering a polynucleotide into human stem cells for treatment or prevention of a disease or condition. In one aspect, vector system is disclosed that comprises a human sperm cell linked to a polynucleotide through a linker. The human sperm cell may be used to introduce the polynucleotide into a human oocyte during fertilization. The resulting zygote may then be cultured, differentiated, and transplanted into the human body.

GENERAL DESCRIPTION OF THE PREFERRED EMBODIMENTS

Generally, a method and system for delivering a particular polynucleotide into a human stem cell for treatment or prevention of a disease or condition is described. The method uses human sperm cells that are linked to a particular polynucleotide to introduce the polynucleotide into a human oocyte during fertilization. The resulting zygote, which is a totipotent stem cell, may then be cultured into embryonic stem (ES) cells, which are pluripotent stem cells. The ES cells may be further differentiated into specific cell types and used as graft cells for transplantation into a particular human host or patient. The polynucleotide may be a DNA molecule or a gene, which preferably encodes for a particular gene product such as a protein or anti-sense RNA. The gene product in turn may alleviate, treat, or prevent a disease or condition of the human host. Alternatively, the polynucleotide may also include a gene that has been knocked out, e.g., by inserting a neomycin gene or any other antibiotic or selection marker gene into the gene to be knocked out; thereby disrupting the gene. This knocked out gene may be used to replace the endogenous gene, thereby eliminating the production of a gene product that is normally produced by the cell.

To increase the chances of immunological compatibility of the graft ES cells, it may be preferred, but not required, that the sperm cells and oocytes be isolated from the biological parents of the human host. The sperm cells or oocytes may also be isolated from the human host, depending if the host is a male or female, and fertilized with corresponding oocytes or sperm cells from a close relative. If the biological parent or close relatives are not available, the sperm cells or oocytes may be isolated from any human adult.

Examples of human diseases or conditions that may benefit from delivery of a therapeutic gene or polynucleotide into a human host via the ES cells include (1) genetic disorders such as sickle cell anemia, thalassaemia, Gaucher disease, ADA deficiency, etc.; (2) muscular or neuro-related diseases such as muscular dystrophy, Alzheimer's, Parkinson's, neural injury, ischemia, stroke, etc.; (3) hormone or growth factor deficiency such as diabetes (insulin), anemia (erythropoietin), hemophilia (factor 8 or 9), etc.; or (4) any other condition for which the introduction of a therapeutic gene or inhibition of an endogenous gene through anti-sense or knockout may be helpful. Microbial or cancer antigen genes may also be used and delivered into the resulting ES cells by the sperm-linked-DNA complex to form vaccines against infectious agents or cancer cells.

Figure 1:
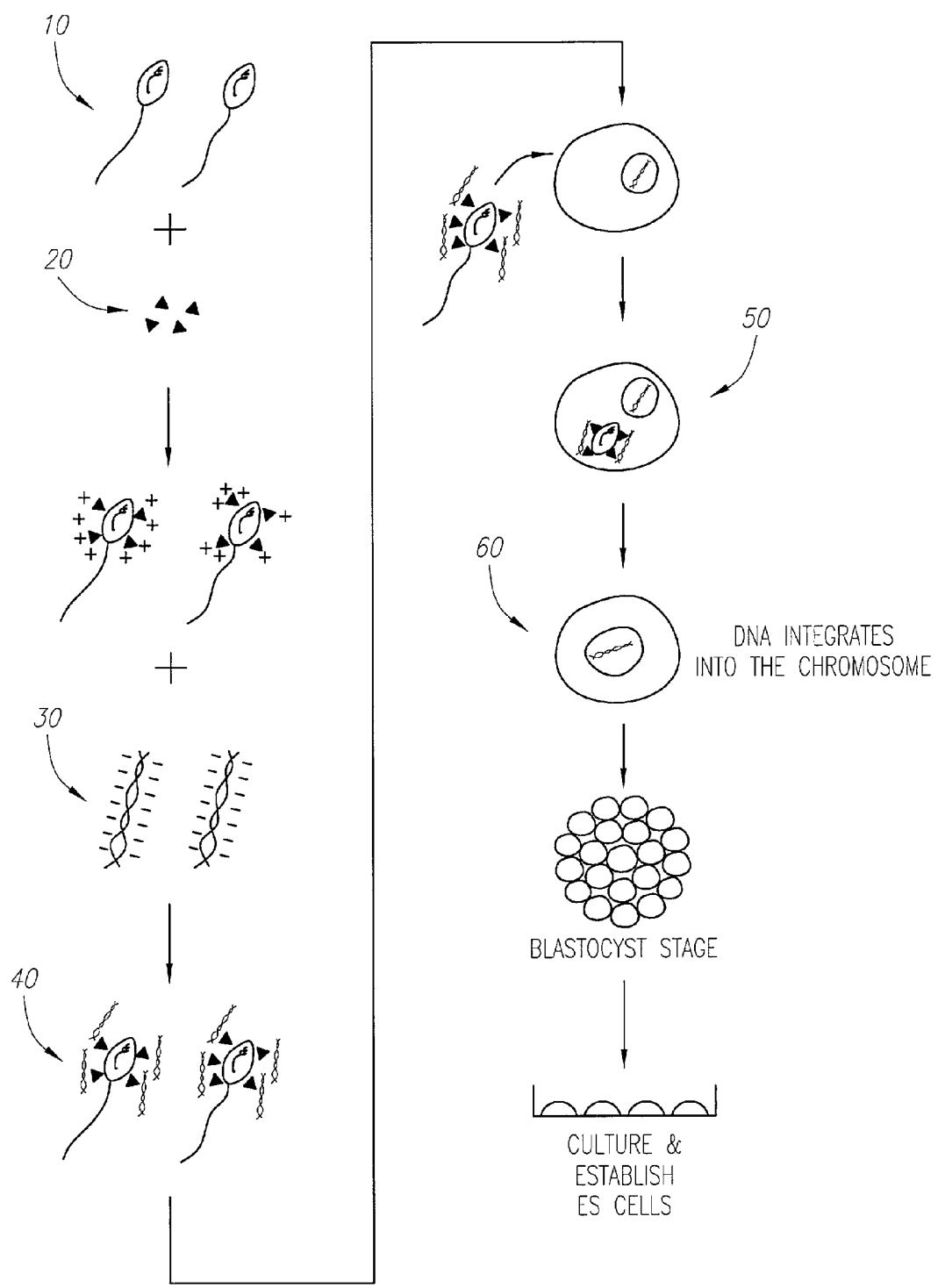
FIG. 1 is a pictorial representation of the basic steps involved in introducing an exogenous polynucleotide into an embryonic stem cell using a sperm cell.

FIG. 1 shows the basic steps involved in using a sperm cell to deliver an exogenous polynucleotide into an oocyte forming a zygote that may be cultured into Embryonic Stem (ES) cells. Briefly, sperm cells 10 may be collected from any human male and are bound together with linkers 20. The linkers are preferably antibodies or immunoglobulins of the types, IgG, IgA or IgM, but they can also be other compounds such as peptides, glycoproteins, carbohydrates, or other chemical-compound linkers. The linkers bind or associate to the sperm cells' external surface through different molecular interactions such as ionic interaction, covalent bonds, Vander Waals forces, or ligand-receptor interaction. Circular or linear polynucleotides or DNA molecules 30 may then bind or attach to the linkers on the sperm-linker complex also through different molecular interactions such as ionic, covalent bonds, Vander Waals forces, or ligand-receptor interaction. The DNA molecules may encode for certain gene products, but they may also be disrupted genes, homologous with endogenous genes, that recombine into the chromosome to knockout a gene. The DNA molecules may further encode for an anti-sense RNA complimentary to an endogenous messenger RNA in the cell to repress the translation of that messenger RNA.

Alternatively, the linker may also be linked first with the DNA molecules to form a linker-DNA complex before being applied to the sperm cells. An example of the linker-DNA complex is an antibody attached with DNA molecules where the antibody specifically recognizes certain surface epitopes on sperm cells. Because of the acidic characteristic of naked DNA, it can ionically associate, bind, or couple with an antibody that has basic or positively charged properties. However, the DNA-linker interaction is not limited to ionic interaction. The complex can also be crosslinked by UV light to form covalent bonds by well known methods in the art. Both the DNA and the linker can also be modified by methods known in the art. For example, the DNA can be biotinylated by adding biotinylated deoxynucleotides in a PCR reaction or other DNA synthesis reaction; the antibody can be modified or purchased with attached strepavidin, which binds tightly to the biotin on the DNA. Alternatively, a secondary antibody, which is modified with strepavidin and recognizes the first antibody can also act as a secondary linker between the modified DNA and the first linker.

Preferably, the DNA molecule introduced into the ES cell includes a suitable promoter for expressing a desired gene in the cells. The promoter may be constitutive, i.e. allowing expression of a gene product all the time, or may be a tissue specific promoter such as a promoter for skeletal muscle α-actin, β-globin locus control region (LCR), or for platelet derived growth factor β-chain. The promoter may also be an inducible type promoter that may be induced by hormones, drugs, minerals, or other compounds. An example of inducible type promoter may be a mouse metallothionein promoter responsive to zinc as described and used in U.S. Pat. No. 6,063,630, which is hereby incorporated by reference as if fully set forth herein. Other examples may include tetracyline inducible promoter, estrogen inducible promoter, ecdysone inducible promoters, or any other suitable inducible promoters. It is also preferred that the DNA molecule includes a selection gene or an antibiotic resistant gene such as neomycin, hygromycin, puromycin, or other suitable antibiotic resistant genes that are used for selecting the cells that have integrated the DNA into their chromosome.

After the sperm-linker-DNA complex 40 has formed, the complex 40 can then be used to effectuate in vitro fertilization (IVF) using well known techniques currently used in fertility clinics. Upon fertilization, the DNA is introduced into the zygote 50, which may further differentiate into a blastocyst 60 having the DNA molecule integrated into the chromosome of the cells. The blastocyst cells may then be dissociated and plated onto a petri-dish with an appropriate feeder cell layer such as growth arrested mouse embryonic fibroblasts. The blastocyst cells may further divide into embryonic pluripotent cells (ES stem cells). If an antibiotic resistant gene is introduced, the blastocyst cells may be grown to a certain desired number or concentration before the applying the selection via the antibiotic.

In practice, it may be preferred to fertilize multiple oocytes with multiple batches of sperm cells linked with particular DNA molecules. The resulting blastocyst cells or ES stem cells may then be screened for immunological compatibility with the human host recipient of the graft ES cells. Screening for immunological compatibility may include, for example, determining the particular Human Leukocyte Antigen (HLA) type, or other suitable immunological markers of the cells as compared with the human host recipient. HLA typing, for example, has been routinely used to determine the compatibility of bone marrow donors and recipient. HLA typing of the ES cells may utilize DNA-based approach such as the Sequence Specific Oligonucleotide Probe Hybridization (SSOPH) or Sequence Specific Primer Typing (SSP). Hurley, C. K., et. al. (1997) "HLA Typing by Molecular Methods," *Manual of Clinical Laboratory Immunology*. 5th ed, Rose, N. R., Conway de Macario, E., Folds, J. D., Lane, H. C., Nakamura, R. M. ed., Washington: ASM Press 1997: 1098–1111, which is hereby incorporated by reference. For the human host, HLA typing may also utilize SSOPH or SSP, or conventional serological typing using the microcytotoxicity assay. An example of a DNA based approach to screen for immunological compatibility of embryos formed by IVF is the October 2000 birth of Adam Nash of Colorado and the transplantation of his hematopoietic stem cells to his sister Molly Nash. Adam Nash was formed in vitro and was genetically screened to be immunologically compatible with his sister Molly Nash, who suffered from leukemia. See Weiss, R., "Test-Tube Baby Born to Save Ill Sister; Genetic Selection by Colorado Parents May Herald a new Era" *The Washington Post*, Oct. 3, 2000.

After screening of a suitable ES cell line that is immunologically compatible with the human recipient of the graft, the ES cells may then be differentiated into appropriate cell types for transplantation into the human body. For example, ES cells may be differentiated to myoblast or muscle stem cells, which may express and secrete a particular protein such as insulin, or erythropoietin encoded by the DNA molecule or polynucleotide. The myoblast cells may then be transplanted into the skeletal muscles to further differentiate inside the body and to express the particular gene product or secrete the particular protein into the human blood system.

The following demonstrate various examples of this method and system to deliver a therapeutic gene into the human stem cells derived from fertilization of an oocyte with a sperm-linker DNA complex. Methods in molecular genetics, flow cytometry, antibody production, hybridoma technology, in vitro fertilization, and embryo manipulation, used but not explicitly described in this disclosure had already been amply reported in the scientific literature. These methods are well within the ability of one skilled in the art.

EXAMPLE I

Human oocytes may be collected from an adult female that preferably has given appropriate informed consent to the use of the oocytes. Techniques for manipulation of human oocytes are well known in the art of infertility treatment. Briefly, ovarian hyperstimulation may be initiated with leuprolide acetate (Lupron; TAP Pharmaceuticals, North Chicago, Ill.) and administered from the midluteal phase at 1.0 mg/day subcutaneously for 10 days. The dosage may then be reduced to 0.5 mg/day until the morning of human chorionic gonadotropin (hCG) injection. After pituitary down-regulation of estrogen, human menopausal gonadotropin may be given until at least two follicles have reached a mean diameter of 1.8 cm. Oocyte retrieval may be scheduled for 35 hours after the hCG injection.

Human sperm cells may be collected from an adult male that preferably has also given appropriate informed consent to the use of his sperm cells. The ejaculated sperm cells may be collected and prepared with a 50-70-95 discontinuous Percoll gradient or a mini-Percoll method, depending on the initial semen parameters. After retrieving the pelleted sperm cells, the sperm cells may be washed with modified G1 medium supplemented with 5 mg/ml human serum albumin (HAS; Irvine Scientific, Santa Ana, Calif.). Composition of the G1 media is set out in Table 2 below. Modified G1 media contains a glucose concentration of 3.15 mM and lacked both EDTA and glutamine. Gardner, D. K. et. al., (1998) "Culture and transfer of human blastocysts increases implantation rates and reduces the need for multiple embryo transfers," *Fertility and Sterility* 69(1): 84–88. This reference is hereby incorporated by reference as if fully set forth herein.

EXAMPLE II

This example illustrates the ability of the linker antibody, mAbC, that is secreted from the hybridoma cell line assigned the deposit designation number PTA-6723, deposited on May 24, 2005 with the American Type Culture Collection, 10801 University Boulevard, Manassas, Va. 20110-2209, to bind to human sperm cells. Briefly, human sperm cells were incubated with the different primary monoclonal antibodies, washed, and further incubated with a secondary antibody that specifically recognized mouse immunoglobulin. This secondary antibody, which was commercially available and well known in the art, had fluorescent molecules such as fluorescein or rhodamine conjugated to it. Once the secondary antibody molecules were bound and washed, a flow-cytometry instrument or a FACS sorter counted the number of fluorescent sperm cells with bound primary and secondary antibodies from naked sperm cells.

Figure 2:
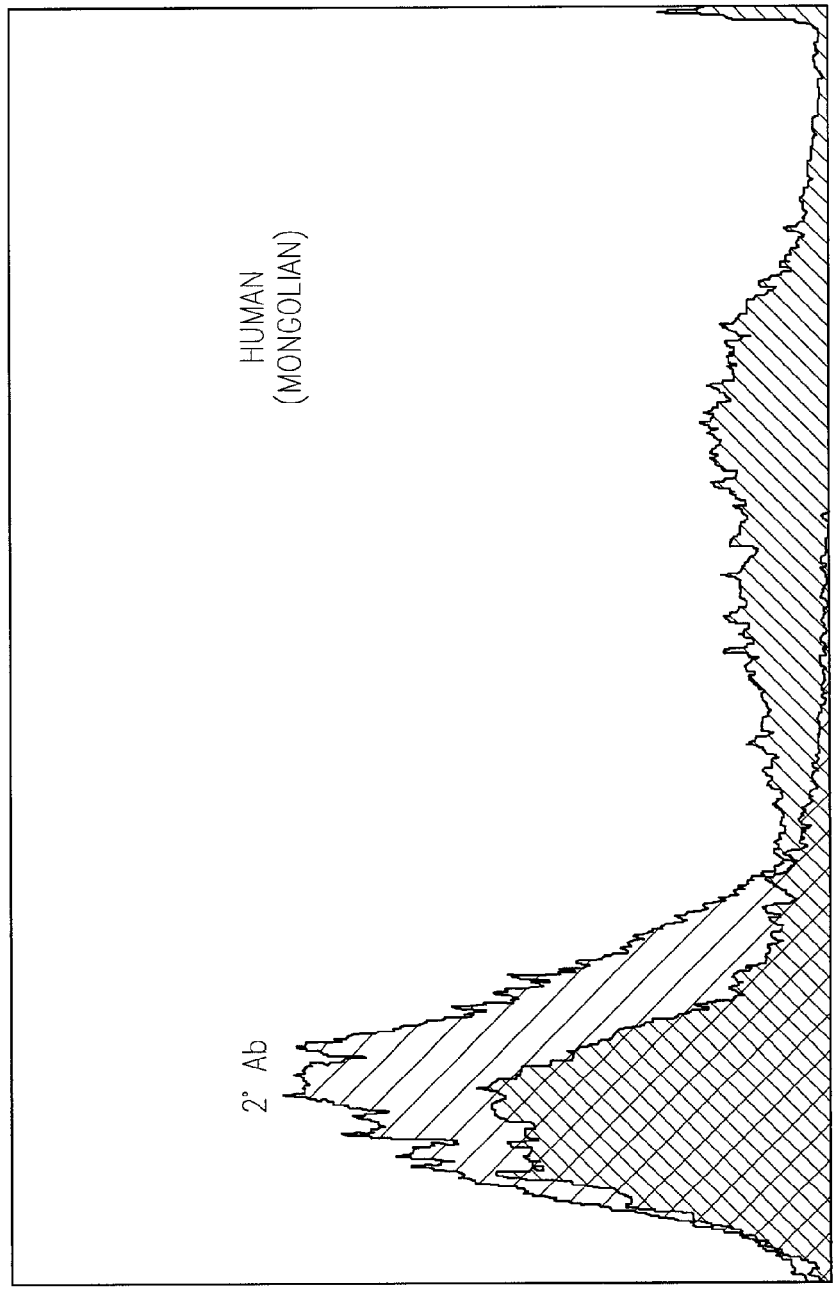
FIG. 2 shows a flow-cytometry result of binding a sperm-specific antibody to human sperm cells.
Figure 3:
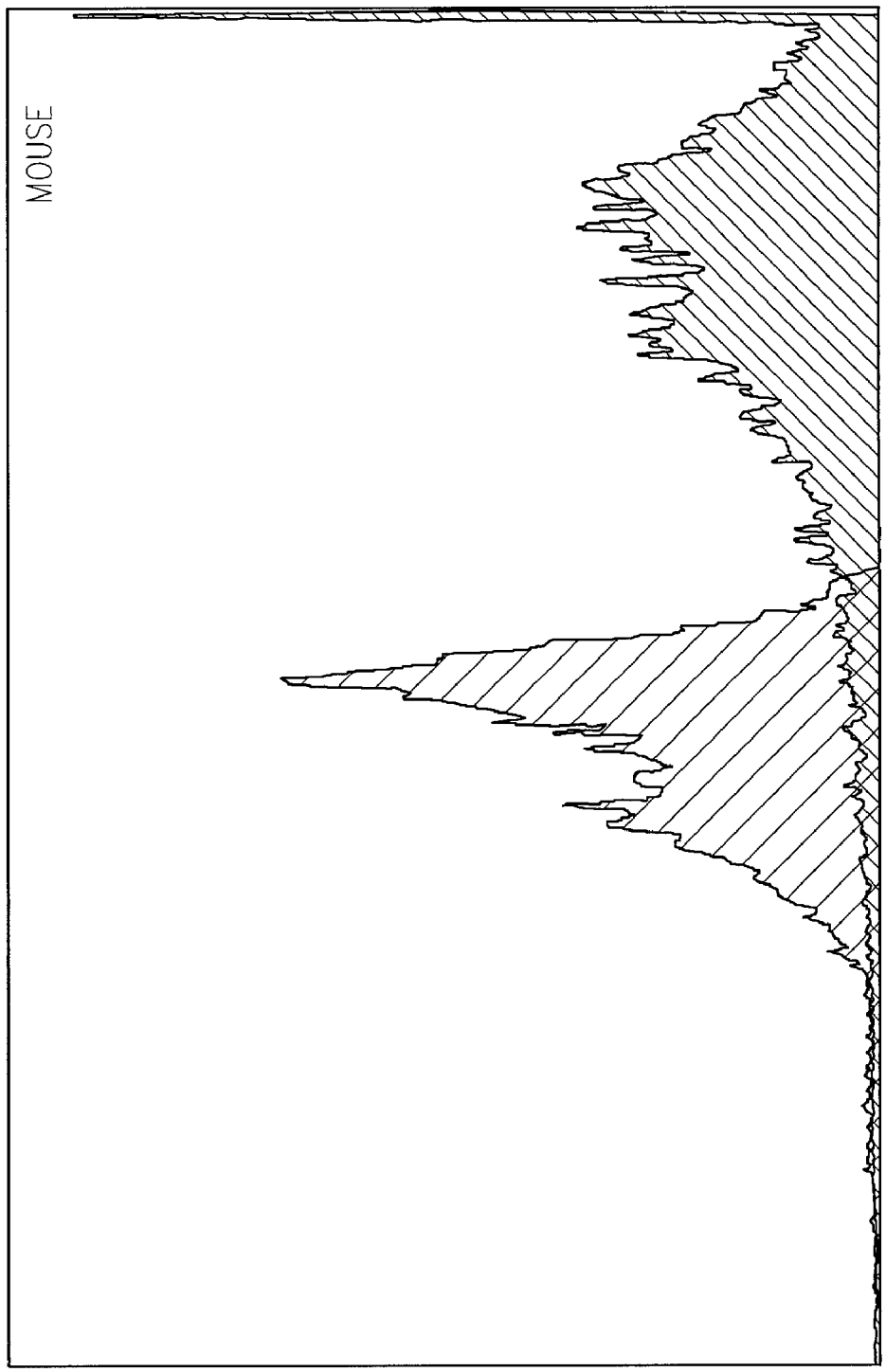
FIG. 3 shows a flow-cytometry result of binding a sperm-specific antibody to murine sperm cells.
Figure 4:
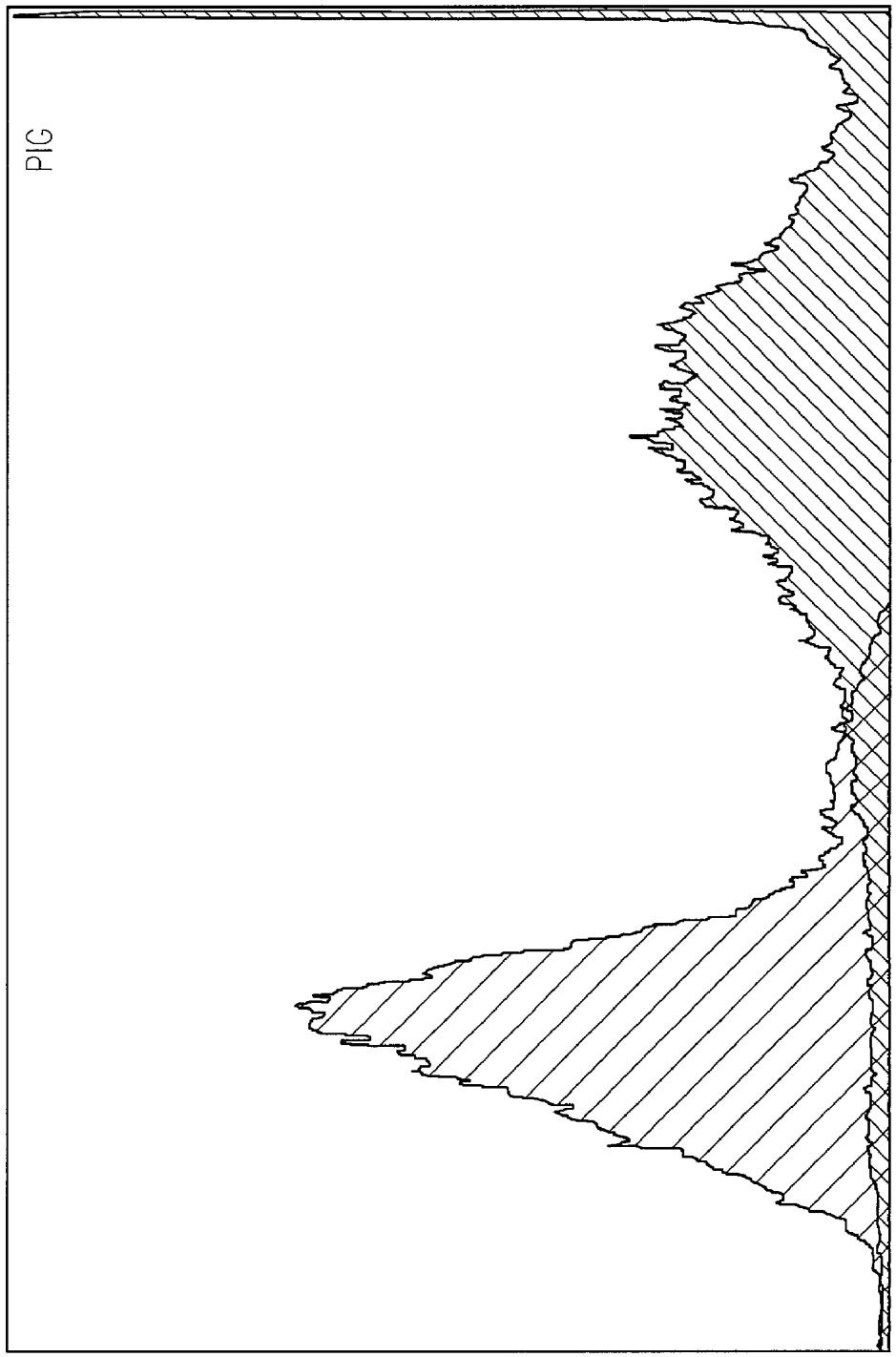
FIG. 4 shows a flow-cytometry result of binding a sperm-specific antibody to pig's sperm cells.

FIGS. 2–4 show flow-cytometry analyses for mAbC, linker antibody that binds to the sperm cells from human, mouse, and pig, respectively. mAbC also binds to the sperm cells of cow, chicken, goat, and sheep, which are disclosed in U.S. patent application Ser. No. 09/537,861. The Y-axis of the figures corresponds to the number of sperm cells detected while the X-axis is the relative intensity of fluorescence bound to the cell. Cross-lined peaks denote control reactions where the sperm cells were incubated only with the fluorescent anti-mouse immunoglobulin antibody. On the other hand, the shaded peaks denote the reactions where mAbC antibody and the secondary antibody were incubated with corresponding sperm cells in a human, mouse, and pig, respectively. Right shifts in the peaks denote positive binding of the mAbC antibody.

As can be seen in FIG. 2, greater fluorescence signals can be detected from a certain population of human sperm cells incubated with mAbC and the fluorescent secondary antibody (right shaded peak) as compared with human sperm cells incubated with the fluorescent secondary antibody alone (left cross-lined peak). Thus, FIG. 2 shows that mAbC binds specifically to certain antigens expressed in the outer surface of a certain population of human sperm cells. Similarly, in FIGS. 3 and 4, greater fluorescence can be detected from mouse and pig sperm cells, respectively, incubated with mAbC and the fluorescent secondary antibody as evidenced by the right shaded peaks. The shifts in fluorescence peaks upon addition of mAbC clearly demonstrate the affinity of the mAbC antibody to sperm cells from human, mouse, and pig.

DNA binding assays were also performed to further show the ability of mAbC to associate or link DNA molecules with sperm cells. Briefly, DNA molecules were labeled with $p^{32}$ using standard end labeling techniques with T4 DNA polymerase and were incubated with mouse, pig, chicken, sheep, goat, cow, and human sperm cells together with either mAbC, or a control antibody specific to a Drosophila protein. The amount of DNA binding was measured by scintillation counting.

As shown in Table 1 below, sperm cells incubated with mAbC significantly bound more labeled DNA compared with reactions with no antibody or with the Drosophila protein-specific antibody. Reactions 1 and 2 contained only sperm cells and labeled DNA, while reactions 3 and 4 contained the Drosophila-protein-specific antibody together with sperm cells and labeled DNA. Reactions 6 and 7 contained mAbC together with sperm cells and labeled DNA.

EXAMPLE III

This example illustrates the in vitro fertilization (IVF) procedure and the culturing of the resulting zygotes into embryonic stem cells. Human sperm cells may be incubated with the mAbC linker and any DNA molecule using similar techniques as described in mouse and pigs. IVF of the isolated human oocytes may then be performed with the human sperm-linker-DNA complexes using procedures routinely used in fertility clinics.

Resulting zygotes may then be cultured into human blastocysts using G1 media from day 0 to day 3 and switching to G2 media from day 3 to 5, as reported by Gardner, supra. Table 2 provides the composition of Gardner's G1 and G2 media based on Barnes, F. L., et. al. (1995) "Blastocyst development and pregnancy after in vitro maturation of human primary oocytes, intracytoplasmic sperm injection and assisted hatching," *Human Reproduction*, 10:3243–3247, which is hereby incorporated by reference in its entirety as if fully set forth herein.

Concentrations for non essential amino and essential amino acids in G1 and G2 medium are in the same concentration as disclosed in Eagle, H. (1959) "Amino acid metabolism in mammalian cell cultures," *Science*, 130: 432–437, and is provided in Table 3.

Briefly, fertilized eggs, i.e., embryos with two pronuclei may be collected and cultured in 1 mL of G1 medium for 48 hours, which is day 3 of development where the embryo is at the 4–8 cell stage. On day 3, the embryo may be transferred to 1 mL of G2 medium and further cultured for another 48 hours. After reaching the blastocyst stage, embryonic cells may be further cultured into ES cell lines as described in Thomson, J. A., et. al., (1998) "Embryonic Stem Cell Lines Derived from Human Blastocysts," *Science* 282:1145–1147; Thomson, J. A., et. al. (1995) "Isolation of a primate embryonic stem cell line," *PNAS*, 92: 7844–7848, which are hereby incorporated by reference as if fully set forth herein. Briefly, inner cell masses of the blastocysts may be isolated by immunosurgery with a rabbit antiserum to BeWO cells, and plated on growth arrested (irradiated or chemically treated) mouse embryonic fibroblasts (which may be commercially obtained from Incyte Genomics, Palo Alto, Calif.) in high glucose DMEM without pyruvate (Life Technologies, Bethseda, Md.) supplemented with 20% fetal bovine serum or fetal cord serum, 1 mM glutamine, 0.1 mM β-mercaptoethanol and 1% nonessential amino-acid stock (Life Technologies).

After 9 to 15 days, outgrowths from the inner cell mass may be dissociated into clumps by exposure to 1 mM EDTA in $Ca^{2+}/Mg^{2+}$ free phosphate-buffered saline, or by exposure to dispase (10 mg/ml from Sigma Chemicals, St. Louis, Mo.), or by mechanical dissociation with a micropipette. The resulting clumps, preferably having 50–100 cells, may be replated onto the growth arrested mouse embryonic fibroblasts in fresh medium. Colonies having undifferentiated morphology may form clumps and may be selected and dissociated to expand the number of cells. Once established, cultures may be passaged by exposure to type IV collagenase (1 mg/mL, Life Technologies) or by selection of individual colonies by micropipette.

EXAMPLE IV

After the establishment of an ES cell line, the ES cells may be differentiated into various cell types for transplantation into the human body. For example, the ES cells may be differentiated into hematopoietic cells for bone marrow transplantation, neural cells for transplantation into the central nervous system, muscle cells for transplantation into skeletal muscles, or any other cell types.

Recent reports have shown that human ES cells may be differentiated in vitro by treatment with various growth factors. Schuldiner, M., et. al., (2000) "Effects of eight growth factors on the differentiation of cells derived from human embryonic stem cells," *PNAS*, 97:21, pp. 11307–11312. This reference is hereby incorporated by reference as if fully set forth herein. In particular, human ES cell lines may be grown on mouse embryo fibroblasts in 80% KnockOut DMEM (Life Technologies), 20% KnockOut SR (Life Technologies), 1 mM glutamine, 0.1 mM b-mercaptoethanol, 1% nonessential amino acid stock, 4 ng/ml basis fibroblast growth factor (bFGF), and $10^3$ units/ml leukemia inhibitory factor (LIF). To initiate differentiation, the ES cells may be initially induced to form embryoid bodies (EBs) by transferring to a petri dish with the same culture medium, but without the LIF and bFGF. EBs include the three embryonic germ layers, endoderm, mesoderm, and ectoderm, that give rise to all of the various cells and tissue in the body. The EBs may be cultured for five days and then dissociated with trypsin. The resulting cells may then be plated on fibronectin (50 µg/ml) coated petri dish or on suitable feeder cell layer that have been treated with mitomycin C. The dissociated and plated cells may be incubated with different growth factors to further enrich for the desired cell type.

For example, myoblasts or muscle progenitor cells may be enriched by addition of Activin A (~20 ng/ml) and/or TGF-β and grown for additional 5–10 days. Id.; See also Rohwedel, J., et. al., (1994) "Muscle Cell Differentiation of Embryonic Stem Cells Reflects Myogenesis in Vivo: Developmentally Regulated Expression of Myogenic Determination Genes and Functional Expression of Ionic Currents," *Developmental Biology*, Vol. 164, pp. 87–101, which described the differentiation of mouse ES cells into myoblasts by treatment with Activin-A; and Slager, H. G., et. al., (1993) "Transforming Growth Factor-β in the Early Mouse Embryo: Implications for the Regulation of Muscle Formation and Implantation," *Developmental Genetics*, 14:212–224, which described the differentiation of mouse ES cells into myoblasts by treatment with TGF-β. The Rohwedel and Slager references are hereby incorporated by reference as if fully set forth herein.

Neural cells, on the other hand, may be enriched by incubating the dissociated cells from the EBs with Retinoic Acid (RA) (~10 µM) for 5–10 days or longer. Schuldiner, supra; See also Bain, G., et. al., (1995) "*Embryonic Stem Cells Express Neuronal Properties in vitro,*" *Developmental Biology*, 168:342–357, which described the differentiation of mouse ES cells into neurons by treating with retinoic acid; and Instruction Manual for NT2 Precursor Cells available from Stratagene Cloning Systems, La Jolla, Calif., Catalog # 204101, Revision #079006, which details long term (6 weeks) culture conditions for retinoic acid differentiation of a human teratocarcinoma cell line into neuronal cells. The Bain reference and the Instruction Manual from Stratagene are hereby incorporated by reference as if fully set forth herein.

As to enrichment of hematopoietic stem cells (HSC) that may be able to repopulate the bone marrow in vivo, the cells derived from the EBs may be treated with recombinant interleukin 3 (rIL-3) (~100–300 units/ml), recombinant interleukin 6 (rIL-6) (~10–50 units/ml) and cell free supernatant from fetal liver stromal cell line as described in Palacios, R., et. al., (1995) "In vitro generation of hematopoietic stem cells from an embryonic stem cell line," *PNAS*, 92: 7530–7534, The Palacios reference described the generation of mouse HSC from mouse ES cells and is hereby incorporated by reference as if fully set forth herein. In enriching for the HSCs, it may be also be preferred to co-culture the ES cells with mitomycin-C treated bone marrow stromal cells as described in Palacios, supra, or stromal cells derived from the aorta-gonad mesonephros (AGM) region of a 10.5 day postcoitum mouse embryo as described in Xu, M. J., (1998) "Stimulation of Mouse and Human Primitive Hematopoiesis by Murine Embryonic Aorta-Gonad-Mesonephros-Derived Stromal Cell Lines," Blood, 92(6):2032–2040, which is hereby incorporated by reference as if fully set forth herein.

It is contemplated that the cultures enriched with the different differentiation factors described above may, in some situations, include mixed population of cells having different development lineages (e.g., myoblasts mixed with neural cells, etc.). Hence, to further purify cells in a specific developmental lineage, differential plating of the cells or flow cytometry sorting of the cells may be needed.

EXAMPLE V

A number of diseases and human conditions arise from the loss of certain secreted protein or hormone naturally produced in the body. The diseases or conditions may result from genetic mutations of the genes or from damage to a particular organ that naturally produce the protein, hormone, factor, or other gene product. For example, in certain cases of diabetes, an individual's own immune system will attack and destroy the body's own β-islet cells, which normally produce insulin. With the destruction of these cells, the body no longer produces adequate insulin to metabolize glucose, which leads to diabetes. Other examples include (1) anemia resulting from loss of secretion of erythropoetin (EPO) in patients with kidney failure or undergoing kidney dialysis, (2) hypothyroidism resulting from loss of thyroid stimulating hormone, (3) hemophilia resulting from lack of Factor VIII or IX, (4) Gaucher disease resulting from lack of glucocerebrosidase, (5) severe combined immunodeficiency (SCID) resulting from mutations in the adenosine deaminase gene, (6) leukocyte adhesion deficiency resulting from mutations in CD 18 cell-surface marker, and any other conditions resulting from deficiency in a secreted factor, hormone, or protein.

Using the linker 20 as described above in FIG. 1, a gene encoding for the needed gene product or protein may be linked to human sperm cells for use to fertilize a human egg in vitro. The gene may be driven by a tissue-specific promoter, constitutive promoter, or inducible promoter. Preferably, a signal sequence for protein secretion naturally associated with the specific gene is included in the polynucleotide used to associate with the sperm cells. Alternatively, an artificial or heterologous signal sequence may be provided upstream of the gene. An example of a signal sequence that may be used is provided in the pSECTag2 vector from Invitrogen, Carlsbad, Calif. In addition, the gene may also be part of a plasmid vector having a antibiotic resistance gene for selection of ES cells having the gene integrated in the chromosome.

After fertilization, establishment, and screening of an ES cell line having the gene, the ES cell line may be differentiated into myoblasts or myocytes and transplanted into skeletal muscles in the human limbs. Alternatively for hematopoietic-type condition, the ES cell line may be differentiated into hematopoietic stem cells and transplanted similar to transplanting stem cells in a bone marrow transplant. Depending on the disease, an ablation of the endogenous bone marrow and hematopoietic cells may be performed by radiation or chemotherapeutic drugs. Once inside the body, the genetically modified cells may secrete the particular protein into the human body to alleviate the condition or disease.

In addition to serving as gene therapy delivery vectors, the genetically altered hematopoietic or muscle cells may also serve as replacement for defective or dying cells. For example, replacement of atrophied muscle cells in Duchenne Muscular Dystrophy (DMD) may be alleviated by transplantation of muscle stem cells.

Similarly, conditions relating to the nervous system such as neurodegenerative disease (Parkinson's, Hungtington's, or Alzheimer's disease) or neural injury related conditions (e.g., ischemia) may be alleviated by introducing neurotrophic factors such as NGF, BDNF, NT3, NT4, CNTF, bFGF, dopamine, etc. Other genes such as genes encoding for apolipoprotein E-e4 and apolipoprotein E-e2 may also be used. Because of the blood brain barrier, it maybe preferable for ES cells transformed with any of these genes to be differentiated in neural stem cells or neurons and transplanted into the affected area of the brain.

In addition to providing neurotrophic factors, the genetically engineered neural-cells transplanted into the central nervous system may also serve as cell-replacement therapy, i.e., the dying neural cells may be replaced with the genetically altered neurons. Techniques for transplantation of neural cells into the central nervous system are described in Neuromethods, Vol. 36: Neural Transplantation Methods, Ed. S. B. Dunnet, A. A. Boulton, and G. B. Baker, Humana Press Inc., Totowa, N.J.

EXAMPLE VI

Vaccination against different infectious agents such as viruses, bacteria or against cancer cells may also be effectuated by linking human sperm cells with a gene encoding for an antigenic determinant of the infectious agents or cells. The resulting ES cells may be differentiated into myoblasts or other appropriate cells and transplanted into the human body. The genetically modified human cells expressing the antigen may elicit immune reaction and the development of antibodies toward the antigens, and thus may protect the body against the infectious agent or cancer cells. For this particular example, HLA screening for immunological compatibility with the patient may not be necessary. The incompatibility of the transplanted cells with the patient may even enhance the patient's overall immune response such that a greater humoral or cellular immune response, or both, to the antigen or cells bearing the antigen is achieved.

EXAMPLE VII

This example demonstrates that a polynucleotide or DNA molecule linked to sperm cells can be introduced into an oocyte resulting in the presence of the polynucleotide in embryonic cells. The polynucleotide is further present and integrated into the chromosomes of adult cells (if the embryonic cells were allowed to fully developed into an animal.) Although this example used mice and pigs to show the introduction of the polynucleotide, one skilled in the art would reasonably understand that human sperm cells linked with the polynucleotide can likewise introduce the polynucleotide into the oocyte through fertilization, and ultimately into the embryonic cells. Furthermore, the data on mice and pigs also show that the polynucleotide or DNA molecules introduced into the embryonic cells are intact and are capable of being expressed and secreted.

EXPERIMENTS WITH MICE

Sperm cells were collected from dissected epididymis of nine to twenty weeks old FVB male mice. Cut into small pieces, these epididymis tissues were incubated in 300 μl of Modified Tyrode's medium at pH 7~8 for one hour to allow the sperm cells to escape into the medium. Once the sperm cells were collected in 300 μl of medium, five micrograms of the linker antibody were added to one million sperm cells at 37° C. for one hour. The sperm-linker complex was washed three times with 300 μl of Modified Tyrode's medium using a standard microcentrifuge set at 3000 rpm for one and a half minutes. The sperm-linker complex was finally resuspended in 300 μl of medium, and one microgram of linearized pCMV-β plasmid or a plasmid encoding for Hepatitis B surface antigen (HBsAg) was added and incubated for one hour.

To collect ovulated mouse oocytes, nine to twelve weeks FVB female mice each received an injection of 5 I.U. Pregnant Mares Serum (PMS) four days before the collection date and another 5 I.U. of human chorionic gonadotropin (hCG) two days before the collection date. Dissected oocytes surrounded by cumulus cells were placed in a 35-mm petri dish containing a drop of Modified Tyrode's medium at room temperature. Afterwards, 300 μl of sperm-linker-DNA complex prepared as described above were added directly to the oocytes. The whole mix was equilibrated with $CO_2$ at 37° C. with mineral oil added on top to prevent evaporation. After four hours of in vitro fertilization at 37° C., the zygotes were collected with capillary tubes and washed thrice with CZB medium. The zygotes were further incubated in 300 μl of CZB medium for 20–22 hrs before being transferred to oviducts of pseudo-pregnant female mice.

Figure 5:
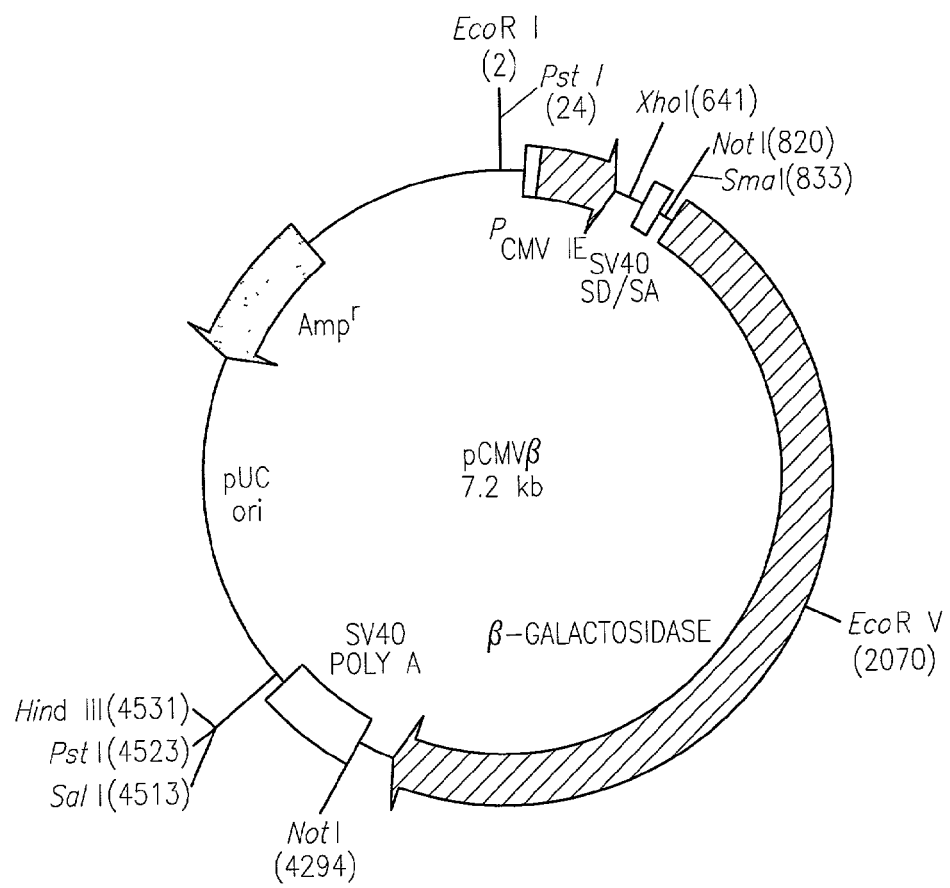
FIG. 5 shows a plasmid map of pCMV-$\beta$.
Figure 6:
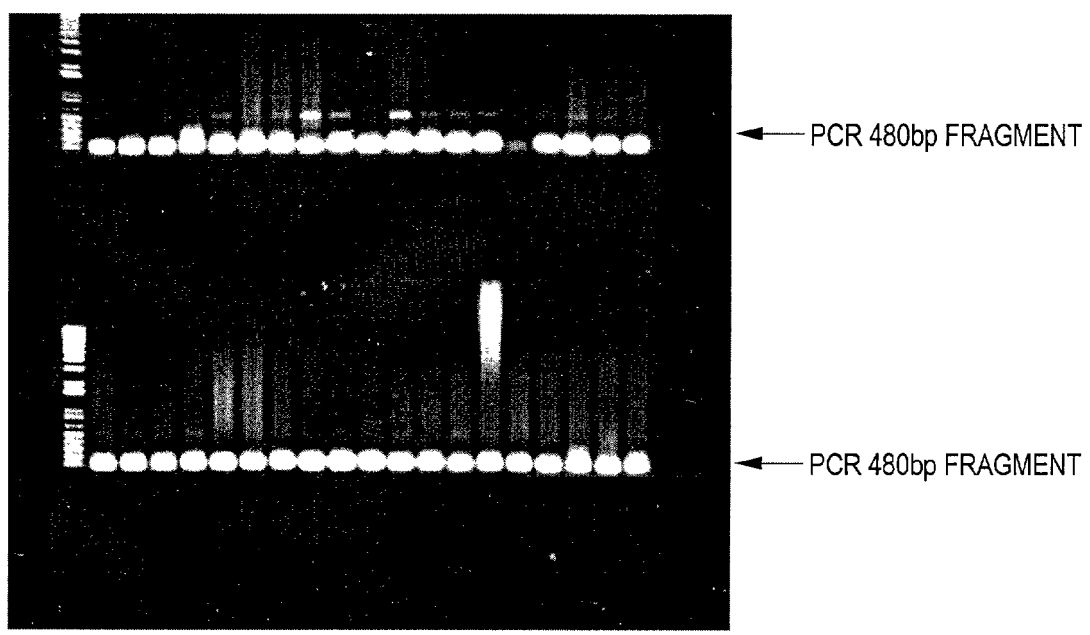
FIG. 6 show results of PCR analysis for the detection of pCMV-$\beta$ sequences in genomic DNA isolated from murine embryos genetically modified according to basic steps in FIG. 1.

To confirm the presence of the pCMV-β plasmid, genomic DNA isolated from embryos, ten days after transplantation into the pseudo-pregnant female mice, were analyzed by PCR using primers that detect a 480 bp fragment corresponding to the CMV promoter region of the pCMV-β plasmid (FIG. 5). In FIG. 6, lanes 6, 7, 8, 9, 10, 12, 13, 14, 15, 17, 18, 19, 24, 33, and 40 clearly show this 480 bp PCR fragment. Lanes 1 and 21 corresponded to the molecular size markers.

Figure 7:
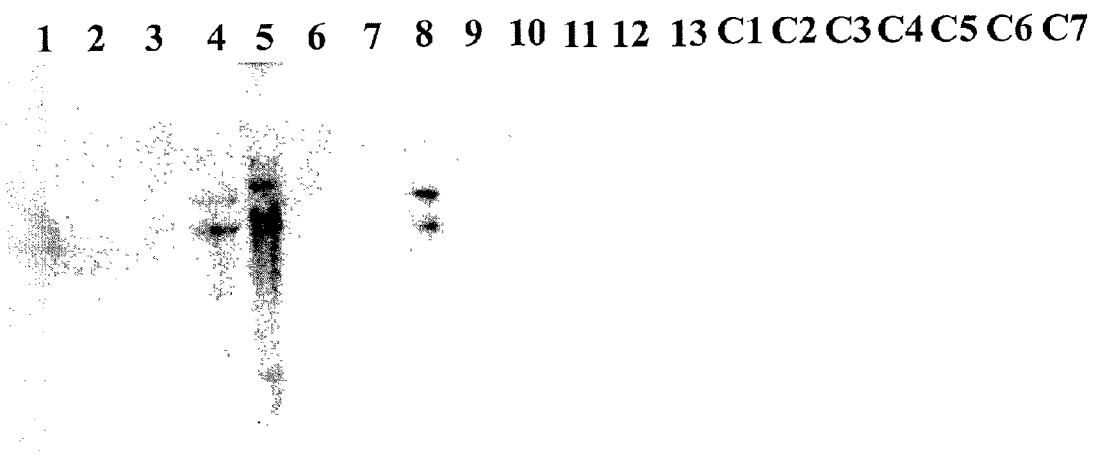
FIG. 7 shows results of southern-blot analysis for the detection of Hepatitis B surface-antigen gene-sequence in mice-tail-genomic DNA with this gene-sequence being integrated into the murine chromosome according to one embodiment of the present invention.

To confirm integration of the HBsAg plasmid into the mice genome, southern blot analysis were also performed. Genomic DNA isolated from mice's tails were digested, ran on a gel, transferred to a nylon membrane according to methods known in the art. FIG. 7 shows the southern blot hybridization results with complementary probe sequences to HBsAg. Lanes 1–13 contained genomic DNA from mice born from pseudo-pregnant mice that received embryos fertilized with the sperm-linker-DNA complex described above; lanes C1–C7 contained genomic DNA from mice that were untreated or non-transgenic mice. Lanes 4, 5, and 8 show bands positive for HBsAg sequences integrated in the mice's genome, thus, demonstrating that three out the thirteen mice were genetically modified.

EXPERIMENTS WITH PIGS

Figure 8:
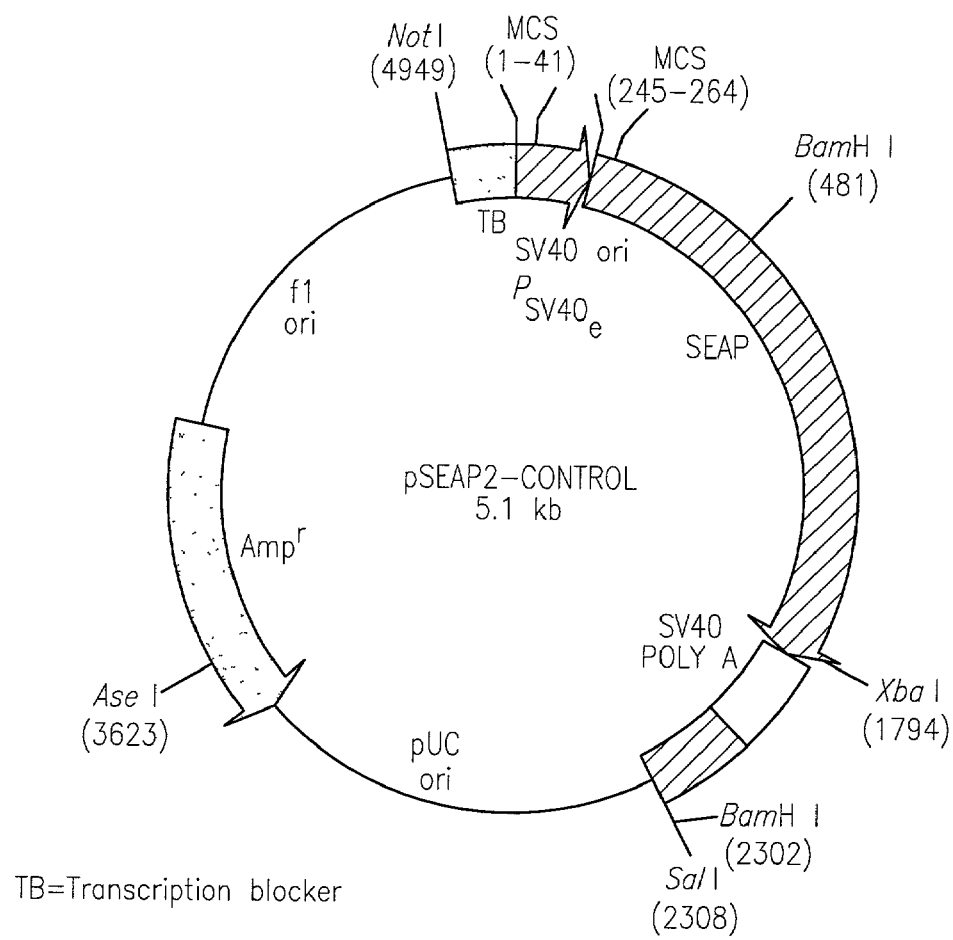
FIG. 8 shows the plasmid map of pSEAP-2-control.

The use of the sperm-linker-DNA complex with pigs will now be described. Ejaculated sperm cells from pigs were collected using methods generally known in the art of animal husbandry. Suspended in one milliliter of pig extender medium (purchased from Merck, Germany, Ref. N.R. 13515/0001—dilute mixture M3 for boar sperm), fifteen million sperm cells were incubated with five micrograms of the linker antibody for forty minutes at room temperature with intermittent shaking in between. After washing the sperm-linker mixture once with pig extender medium and finally resuspending the mixture in 1.5 ml of the same medium, five micrograms of the linearized plasmid pSEAP2-control (FIG. 8, Clontech Laboratories, Inc., Cat. #6052-1) were added and incubated with the mixture for forty minutes at room temperature. Direct injections of 200 μl of the resulting sperm-linker-DNA complex into the oviducts of anesthetized female pigs resulted in fertilization in vivo.

Figure 9:
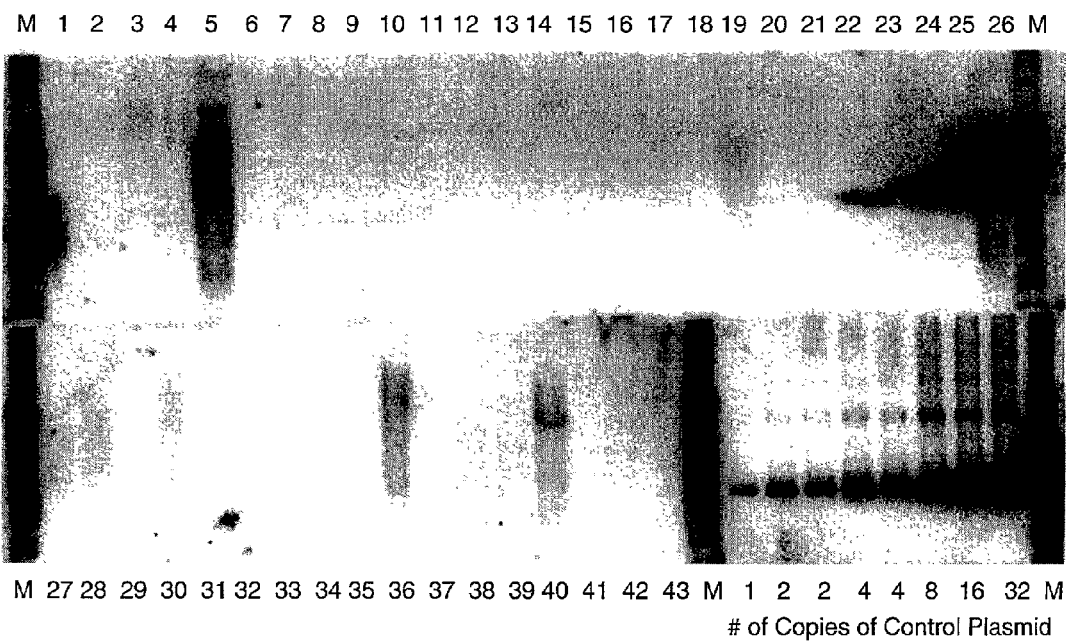
FIG. 9 shows the result of southern-blot analysis for the detection of pSEAP2-control plasmid sequence in the genomic DNA isolated from tail tissues of genetically modified pigs according to one embodiment of the present invention.
Figure 10:
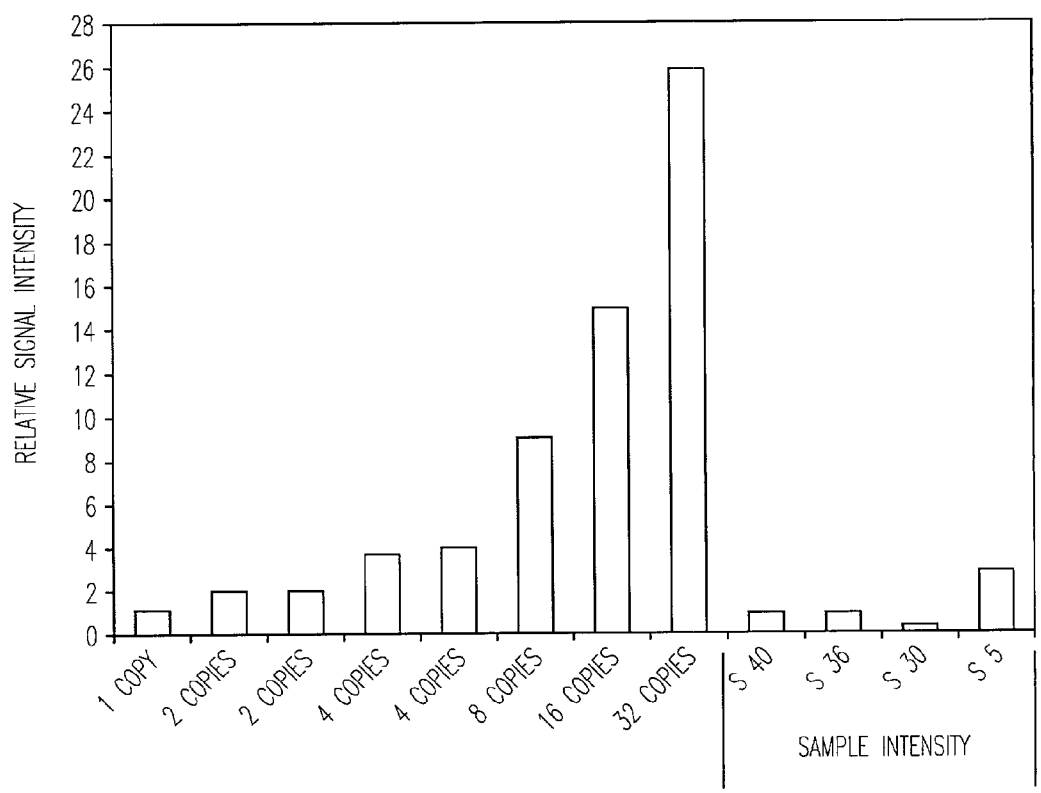
FIG. 10 shows the copy number of integrated pSEAP2-control plasmid in four genetically modified pigs based on densitometric intensities of bands in FIG. 9.

After the pigs were born and grown to 70-day-old pigs, they were analyzed for the presence of the pSEAP2-control plasmid. FIG. 9 shows the southern blot analysis of genomic DNA isolated from the tail tissues of these pigs. Briefly, genomic DNA isolated from these pigs were digested by Not I, run on a gel, and transferred to a nylon membrane according to methods well known in the art. The blot was then probed with labeled sequences from the Not I to BamH I region of the pSEAP2-control plasmid shown in FIG. 8. In FIG. 9, M denotes the marker lanes, and 1–43 denotes the number of pigs analyzed. Hybridization signals in lanes 5, 17, 19, 25, 26, 27, 28, 30, 36, 38, 39, and 40 indicated that the pSEAP2-control plasmid had integrated into the corresponding pig's genome. In the lower right half of the figure, eight lanes with increasing copies of pSEAP2-control plasmid molecules (1, 2, 2, 4, 4, 8, 16, and 32) were also loaded on the gel together with the DNA from the experimental pigs. These eight lanes were used to estimate the copy number of pSEAP2-control plasmid integrated into the pigs based on the densitometric intensities of the bands (FIG. 10). As can be seen in FIG. 10, S5 had the highest intensity, which corresponds to lane 5 of FIG. 9.

Figure 11:
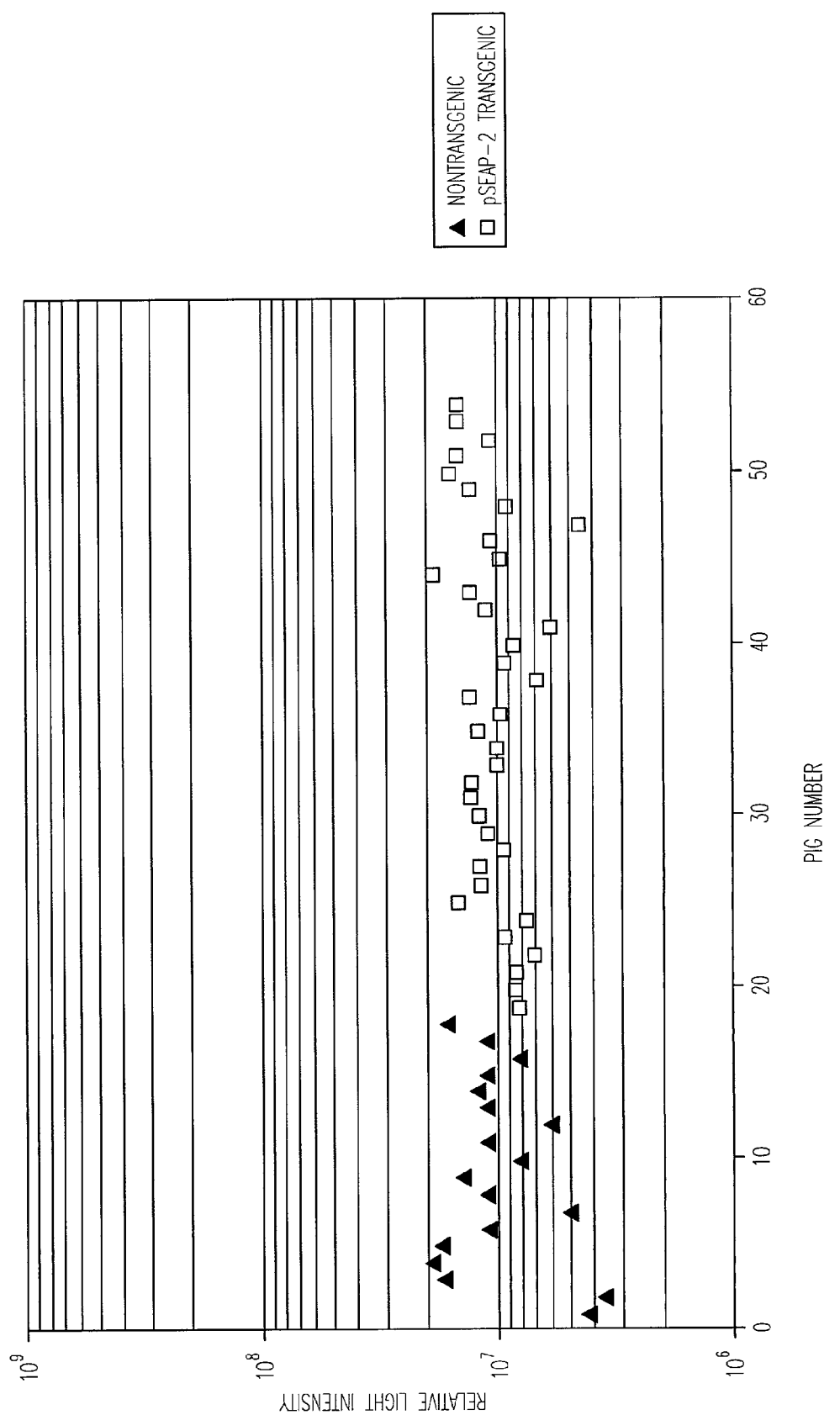
FIGS. 11 and 12 show the results of enzyme assays for secreted alkaline phosphatase found in serum of pigs genetically modified according to one embodiment of the present invention.
Figure 12:
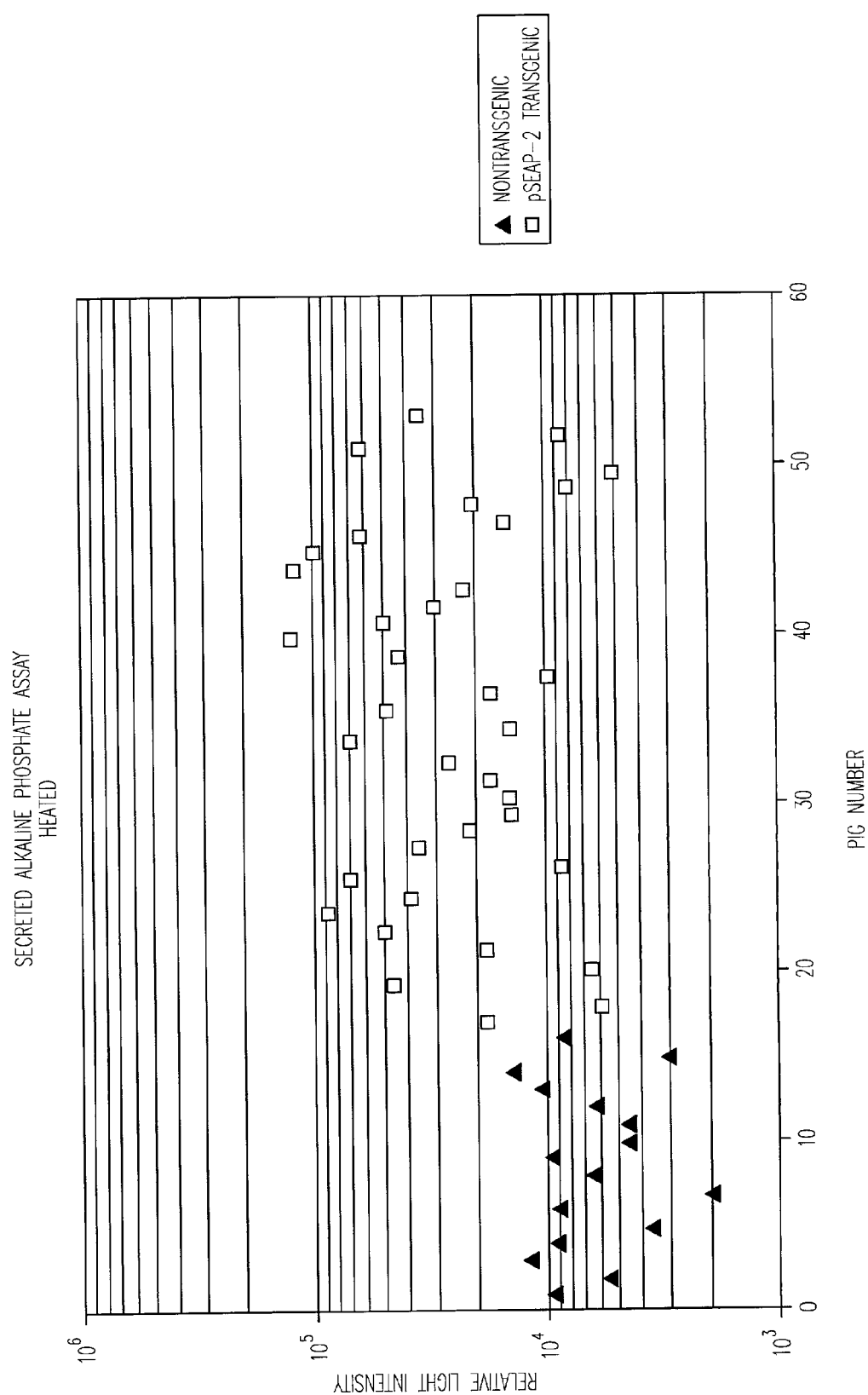

In another study, secreted alkaline phosphatase (SEAP) expressed from the pSEAP2-control plasmid were also detected in 70-day old genetically modified pigs. Serum from these pigs were collected and assayed for SEAP activity using Clontech's Great EscAPE™ SEAP Chemiluminescence Detection Kit (Cat. # K2041-1) and its protocol, which is incorporated herein by reference. The SEAP enzyme expressed from Clontech's pSEAP-2 vector is thermostable. Thus, to determine the level of SEAP activity as opposed to the pigs' endogenous alkaline phosphatase enzyme activity, the assay requires the deactivation of the endogenous alkaline phosphatase enzyme by heating the samples at 65° C. for thirty minutes before adding the chemiluminescence substrate. As a control, FIG. 11 shows the result of the assay without performing this heat deactivation step. The level of total alkaline phosphatase activity was not significantly different between the genetically modified pigs and non-transgenic control pigs. In contrast, FIG. 12 shows the result including this heat deactivation step. Without the endogenous alkaline phosphatase activity, SEAP activity was significantly higher in the genetically modified pigs than in the non-transgenic control pigs. Thus, the pSEAP2-control plasmid had integrated well in the pigs' genome and was actively expressing the SEAP enzyme.

The preceding examples illustrate a method and vector system for introducing a gene into the human body for therapeutic uses. The examples are intended only as examples and are not intended to limit the invention to these examples. It is understood that modifying the examples above does not depart from the spirit of the invention.

TABLE 1

| Reactions | | Mouse (cpm) | Pig (cpm) | Chicken (cpm) | Sheep (cpm) | Goat (cpm) | Cow (cpm) | Human (cpm) |
| --- | --- | --- | --- | --- | --- | --- | --- | --- |
| 1 | no antibody | 12471 | 12971 | 5830 | 15367 | 17749 | 12766 | 10518 |
| 2 | no antibody | 15814 | 13713 | 6383 | 13259 | 16574 | 14398 | 11932 |
| 3 | Control Antibody | 11541 | 10531 | N/D | 14018 | 155347 | 15351 | 9865 |
| 4 | Control Antibody | 13653 | 14038 | N/D | 12834 | 15997 | 13918 | 12357 |
| 6 | mAbC | 18139 | 16269 | 7294 | 19368 | 20385 | 20417 | 16439 |
| 7 | mAbC | 19314 | 17343 | 9865 | 18437 | 19543 | 18643 | 18266 |

TABLE 2

(Composition of G1 and G2 medium)

| Component | G1 medium | G2 medium |
| --- | --- | --- |
| NaCl (mM) | 85.16 | 85.16 |
| KCl (mM) | 5.5 | 5.5 |
| NaH$_2$PO$_4$—H$_2$O (mM) | 0.5 | 0.5 |
| CaCl$_2$—2H$_2$O (mM) | 1.8 | 1.8 |
| MgSO$_4$—7H$_2$O (mM) | 1.0 | 1.0 |
| NaHCO$_3$ (mM) | 25.0 | 25.0 |
| Sodium lactate (60% syrup) (mM) | 21.0 (10.5 L-isomer) | 11.74 (5.87 L-isomer) |
| Sodium pyruvate (mM) | 0.32 | 0.10 |
| Glucose (mM) | 0.5 | 3.15 |
| Glutamine (mM) | 1.0 | 1.0 |
| Taurine (mM) | 0.1 | 0.0 |
| Non-essential amino acids | ALL | ALL others except glutamine |
| Essential amino acids | None | ALL others except glutamine |
| Ethylenediaminetetraacetic Acid (mM) | 0.1 | 0.0 |
| Bovine serum albumin (g/l) | 2.0 | 2.0 |
| Penicillin (g/l) | 0.06 | 0.06 |
| Streptomycin (g/l) | 0.05 | 0.05 |
| Phenol red (g/l) | 0.01 | 0.01 |

TABLE 3

(Concentrations of Essential and Non-essential Amino Acids for G1 and G2 Media)

| Non-essential amino acids | Concentration (mM) | Essential amino acids | Concentration (mM) |
| --- | --- | --- | --- |
| Alanine | 0.1 | arginine | 0.6 |
| Asparagine | 0.1 | cysteine | 0.1 |
| Aspartate | 0.1 | histidine | 0.2 |
| Glutamate | 0.1 | isoleucine | 0.4 |
| Glycine | 0.1 | leucine | 0.4 |
| Proline | 0.1 | lysine | 0.4 |
| Serine | 0.1 | methionine | 0.1 |
| | | phenylalanine | 0.2 |
| | | threonine | 0.4 |
| | | tryptophan | 0.05 |
| | | tyrosine | 0.2 |
| | | valine | 0.4 |

I claim:

1. The monoclonal antibody mAbC, wherein the antibody is characterized by having binding affinity to a sperm cell, wherein the sperm cell bound with the antibody retains the ability to fertilize an oocyte, and wherein the antibody is secreted by the hybridoma assigned ATCC accession number PTA-6723.

2. The hybridoma cell line deposited as ATCC accession number PTA-6723, which produces the monoclonal antibody, mAbC.

\* \* \* \* \*

UNITED STATES PATENT AND TRADEMARK OFFICE
CERTIFICATE OF CORRECTION

| | | |
|---|---|---|
| PATENT NO. | : 7,053,187 B2 | Page 1 of 1 |
| APPLICATION NO. | : 09/781046 | |
| DATED | : May 30, 2006 | |
| INVENTOR(S) | : Kangsheng Wang | |

It is certified that error appears in the above-identified patent and that said Letters Patent is hereby corrected as shown below:

TITLE PAGE, item (73), replace "Gioagri" with --BioAgri--.

Signed and Sealed this

Fifteenth Day of August, 2006

JON W. DUDAS
*Director of the United States Patent and Trademark Office*